United States Patent [19]
Daikuzono et al.

[11] Patent Number: 6,024,738
[45] Date of Patent: Feb. 15, 2000

[54] LASER CATHETER APPARATUS FOR USE IN ARTERIES OR OTHER NARROW PATHS WITHIN LIVING ORGANISMS

[75] Inventors: Norio Daikuzono, Tokyo, Japan; John Vanden Hoek, Florence, Ky.; Kenneth P. Cook, Blue Bell; Robert Bross, Ivyland, both of Pa.

[73] Assignee: Surgical Laser Technologies, Inc., Montgomeryville, Pa.

[21] Appl. No.: 08/893,738

[22] Filed: Jul. 11, 1997

Related U.S. Application Data

[63] Continuation of application No. 08/422,744, Apr. 14, 1995, abandoned, which is a continuation of application No. 08/132,492, Oct. 6, 1993, abandoned, which is a continuation of application No. 07/873,539, Apr. 22, 1992, abandoned, which is a continuation of application No. 07/376,497, Jul. 7, 1989, abandoned.

[30] Foreign Application Priority Data

Jul. 8, 1988 [JP] Japan .................................. 63-171688

[51] Int. Cl.⁷ .................................................. A61N 5/06
[52] U.S. Cl. .................................. 606/7; 606/16; 606/17; 606/28
[58] Field of Search ................................ 606/2, 3–19, 28

[56] References Cited

U.S. PATENT DOCUMENTS

| | | | |
|---|---|---|---|
| 4,592,353 | 6/1986 | Daikuzono | 606/15 |
| 4,648,892 | 3/1987 | Kittrell et al. | 606/7 |
| 4,662,368 | 5/1987 | Hussein et al. | 128/398 |
| 4,693,244 | 9/1987 | Daikuzono | 606/28 |
| 4,736,743 | 4/1988 | Daikuzono | 606/15 |
| 4,773,413 | 9/1988 | Hussein et al. | 128/303.1 |
| 4,848,339 | 7/1989 | Rink et al. | 606/7 |
| 4,849,859 | 7/1989 | Nagasawa | 606/17 |
| 4,860,743 | 8/1989 | Abela | 606/7 |

FOREIGN PATENT DOCUMENTS 2200287 8/1988 United Kingdom .

OTHER PUBLICATIONS

"Physical Properties . . . " by Verdaasdonk et al; Lasers in Med. Sci. vol. 2 No. 183 1987 pp 183–188.
"Laser Angioplasty . . . " by Pilger et al; Cardiovascular Res. 1988 No. 22 pp 146–153.
"Laser Angioplasty's Ingenious Hardware" Cardio. Aug. 1988 pp 45–52.
"Percutaneous Recanalization . . . " by Borst; Lasers in Med. Sci.; vol. 2 1987 pp. 137–151.
"Sapphire and Metal Tip . . . " by Verdaasdonk et al.
"Laser Angioplasty . . . " by Verdaasdonk et al; Lasers in Med. Sci. vol. 2 1987 pp. 153–158.
"Laser Angioplasty . . . " Lammer et al J of Interventional Radiology 1988 p 1–6.
Trimedyne, Inc. brochure P/N 6117.01 Dec. 1987.

*Primary Examiner*—David M. Shay
*Attorney, Agent, or Firm*—Seidel, Gonda, Lavorgna & Monaco, PC

[57] ABSTRACT

A laser catheter for the treatment of lesions and plaque deposits in arteries and other narrow paths having a radiation assembly affixed to a flexible conduit. The conduit generally includes multiple lumens for the passage of an optical fiber, a guide wire, a cooling medium therethrough, or fluid for inflating an angioplasty balloon. The radiation assembly is of short longitudinal profile and includes a generally spherical laser contact member retained within a housing, the latter affixed to the flexible conduit. The radiation assembly provides a dual-mode ablation/melting treatment regime. A longitudinal channel is provided through and along one side of the contact member thereby to permit guide wire positioning of the laser catheter while routing the guide wire away from the laser energy to avoid damage thereto. A balloon, in fluid communication with a catheter lumen, may be positioned rearwardly of the radiation assembly for secondary balloon angioplasty operations.

22 Claims, 6 Drawing Sheets

LASER CATHETER APPARATUS FOR USE IN ARTERIES OR OTHER NARROW PATHS WITHIN LIVING ORGANISMS

This is a continuation of application Ser. No. 08/422,744 filed on Apr. 14, 1995, now abandoned which is a continuation of Ser. No. 8/132,492 filed on Oct. 6, 1993, now abandoned which is a continuation of Ser. No. 07/873,539, now abandoned filed on Apr. 22, 1992, now abandoned, which is a continuation of Ser. No. 07/376,497, filed on Jul. 7, 1989, now abandoned.

BACKGROUND OF THE INVENTION

The present invention relates to equipment for the laser medical treatment of occlusions and lesions in arteries and other narrow regions within living organisms, with particular emphasis on the treatment of human patients. The present invention, while being especially suited for the treatment or removal of plaque and lesions from, for example, the coronary and femoral arteries, finds equal efficacy in many gynecological, urological and other internal procedures requiring narrow path access to the site of treatment.

More particularly, the present invention relates to a laser catheter and laser catheter/balloon angioplasty system for the delivery of laser energy and, more specifically, for the direct contact application of laser energy to the vascular or other site requiring treatment. Use of contact laser technology as a general surgical tool is described in applicant's issued U.S. Pat. Nos. B1 4,592,353; 4,693,244; and 4,736,743.

The treatment of partially or totally occluded arteries due, for example, to cholesterol-triggered plaque deposits has received substantial attention in recent years. Several systems have been proposed in this connection including "hot tips" (the laser or other heating of a metal tip); exposed indirect laser irradiation; and non-directed contact laser treatment. Each of these approaches, however, has failed to fully address one or more of the intrinsic problems associated with narrow path "recanalization" (i.e. the opening of arteries or other narrow channels through the removal of lesions and occlusions). These problems include, for example, the mechanical or thermal perforation of arterial walls; the generation of embolisms due to particles or gas bubbles; and the thermally induced shrinkage of associated walls. The present invention provides an efficacious treatment capability while substantially lowering these adverse risks.

SUMMARY OF THE INVENTION

In a preferred arrangement of the present invention an optically transmissive laser contact member is positioned at the distal end of laser catheter. Contact members of various shapes may be employed, although a spherical member has been found to provide excellent lesion and plaque ablation while subtending a minimum overall length profile.

In this latter connection, it is necessary that the catheter, including the distal end thereof, be highly flexible thereby to enable insertion of the catheter into and through narrow and curved paths. Therefore, one feature of the present catheter is a contact member assembly specifically developed to minimize its overall physical length.

A highly flexible multichannel or multi-"lumen" catheter conduit interconnects the catheter service apparatus (e.g. the laser source) with the distal contact member assembly. This conduit is preferably an extruded polyurethane-nylon blend mixed with barium sulfate for fluoroscopic opacity.

An optical fiber of generally conventional design is routed through one of the catheter lumens terminating rearwardly of the spherical contact member. More specifically, the rearward portion of the contact member is flattened and optically polished to define a laser input surface. The distal end of the optical fiber may be positioned in direct abutting relationship to this input surface or spaced therefrom. In either event, the laser energy from the fiber is substantially fully coupled into the spherical contact member.

In the preferred arrangement of the present catheter, the forward spherical surface of the contact member, i.e. that portion of the contact member that physically engages the lesion to be dissipated, is coated with an infra-red absorbing material thereby directly converting a predetermined percentage of the laser energy emanating the contact member into heat.

The above-described coating, in combination with the spherical or curved forward contact member profile, advantageously generates a dual-mode/dual-phase recanalization regime in which plaque and lesions extending into the artery are effectively ablated while minimizing arterial damage occasioned by undue side radiation or heating of the catheter sides. In this connection, dual-phase refers to the combination ablation caused, firstly, by direct laser irradiation of the tissue and, secondly, by the burning of the tissue in immediate contact with the heated end surface of the contact member. Dual-phase contact laser surgery is described in more detail in U.S. Pat. No. 4,736,743.

The dual-mode or heat accelerated ablation feature of the present invention relates to the temperature and laser radiation gradients found at the forward surface of the contact member and, more specifically, to the formation of two generally distinct ablation regions on the contact member. The first of these regions is defined as the spot directly illuminated by the laser energy coupled into the contact member. By reason of the direct illumination of this forward spot region, and the concomitant heating of that region due to the IR coating thereon, plaque or lesions immediately in contact and forward of this first region are ablated, i.e. dissipated. Importantly, however, the side of the catheter, in the absence of direct laser irradiation thereof, are not heated to ablation temperatures, e.g. greater than 240 degree C, and therefore damage to healthy tissue or arteries necessarily in contact therewith is avoided.

The region immediately adjacent the above-described forward ablation spot defines a second ablation region which does not actually ablate plaque but, due to its proximity to the principal ablation region, and its correspondingly elevated temperatures, literally melts and reforms the plague remaining along the arterial walls as the catheter is urged forwardly therethrough. In this manner, a new channel or enlarged arterial passage is formed through the combination of plaque dissipation and reforming, but in a manner that significantly reduces the peril of arterial damage or perforation.

As previously noted, arterial perforation due either (1) to direct physical pressure while attempting to force a catheter through a narrow and fragile artery; or, (2) to burning occasioned by the misdirected laser irradiation of the artery wall represent significant risks which have heretofor limited the efficacy of narrow path laser recanalization. The present invention minimizes these previously inherent risks as outlined hereinafter.

First, use of the previously discussed dual-mode catheter contact member eliminates laser side radiation and, significantly, reduces and limits the temperatures along the adjacent side regions of the catheter thereby avoiding the problem of side-heating and healthy tissue burning found in certain prior art angioplasty and narrow path catheters, for example, the heated metal "hot tip" catheter.

Second, use of a longitudinally short laser contact assembly in conjunction with a highly flexible catheter conduit results in an overall catheter system better suited for insertion into the sharply radiussed arteries or other paths not-infrequently encountered during medical procedures for which use the present system is intended.

Finally, an eccentric or offset guide wire arrangement is provided to aid in the positioning of the catheter through tight, radiussed, or partially obstructed paths without the application of extreme catheter forces with the attendant risk of physical wall perforation. The guide wire is slidably positioned through a second catheter conduit lumen, forwardly therefrom, through a slot provided in the edge or periphery region of the contact member. In this manner the guide wire is maintained adjacent to the principal area of laser irradiation thereby minimizing the likelihood of guide wire damage occasioned by direct exposure to laser energy. The catheter conduit lumen is preferably offset and aligned with respect to the contact member such that a generally straight channel for the guide wire is provided through the entire catheter assembly.

A separate conduit lumen may be provided for the delivery of liquid to cool and clean the contact member. Alternatively, coolant may share an existing lumen, for example, the optical fiber lumen. In either case, the coolant liquid is generally permitted to exit the catheter through the guide wire slot provided in the contact member. The resulting positive outward flow of coolant further serves to limit entry of blood or other foreign matter to the catheter interior, such entry potentially fouling the optical fiber to contact member interface.

Yet another lumen may be provided through which gas or liquid may be passed to inflate a balloon affixed around the catheter conduit rearwardly of the contact member. In this manner, a multiple step recanalization procedure including laser aided plaque vaporization or reformation followed by balloon angioplasty treatment utilizing the single laser catheter of the present invention.

DESCRIPTION OF THE PREFERRED EMBODIMENT

Figure 1:
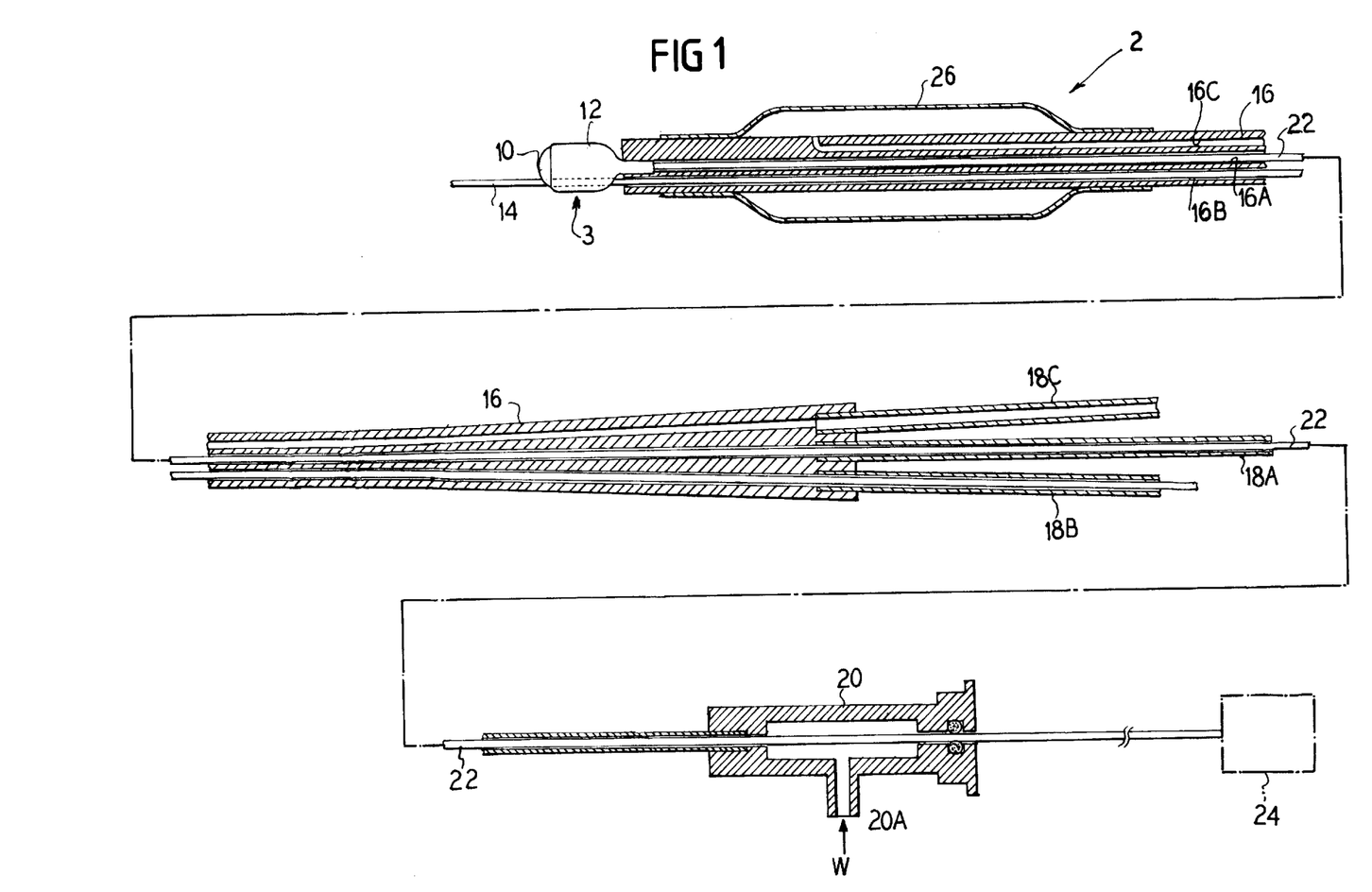
FIG. 1 is a partially sectioned view of the guide wire laser catheter of the present invention taken along the longitudinal axis thereof and illustrated with the balloon angioplasty option.
Figure 2:
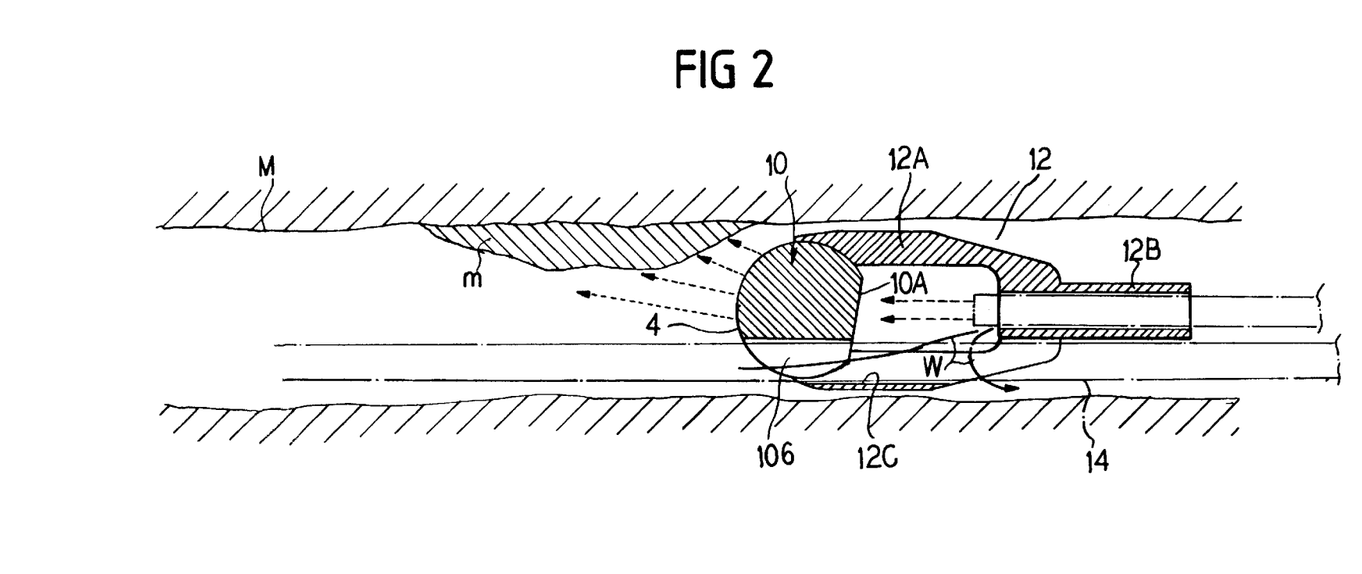
FIG. 2 is a front elevation view, taken in section, of the distal end of the laser catheter of FIG. 1 shown positioned within an artery having a lesion or plaque deposit thereon.
Figure 3:
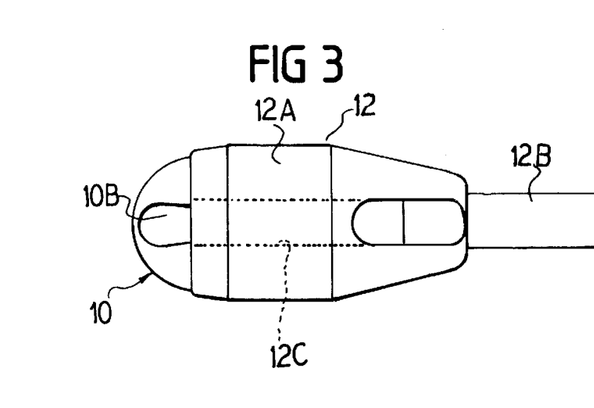
FIG. 3 is a bottom view of the distal end of the laser catheter of FIG. 1 illustrating the eccentric guide wire channel therein.
Figure 4:
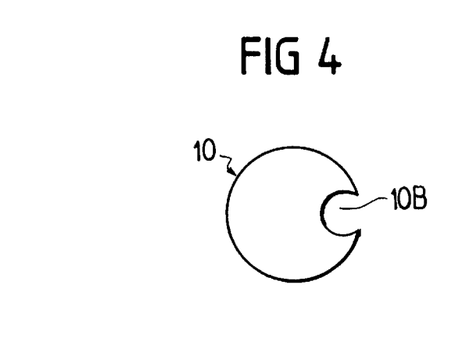
FIG. 4 is a bottom left side view of the laser catheter of FIG. 1 illustrating the offset positioning of the eccentric guide wire channel.

FIG. 1 shows a preferred arrangement of the laser catheter 2 of the present invention with FIG. 2 illustrating the structural details of the distal radiation assembly 3 thereof.

A laser contact member 10 fabricated of a heat resistant and optically transparent ceramic, for example, sapphire, quartz, or fused silica, is rigidly affixed within a housing member 12. The contact member is preferably of spherical shape although other shape configurations, having forward contact surfaces 4 ranging from generally flat to conical, are contemplated hereby.

As best illustrated in FIG. 2, the rear portion of the spherical contact member 10 is flattened and optically polished to form planar a laser input surface 10A through which the laser energy from a laser optical fiber 22 is received. The distal end of the optical fiber may be spaced from the contact member as illustrated or, to minimize the potential for blood or debris fouling the interface therebetween, the fiber may be positioned in abutting contact to surface 10A.

The spherical contact member may be aligned with its input surface 10A oriented perpendicularly with respect to the longitudinal axis of the optical fiber 22 or, alternatively as illustrated in FIG. 2, surface 10A may be offset thereby assuring that the laser energy from the optical fiber will not be normal to the input surface 10A at its point of incidence thereon. When offset as shown in FIG. 2, a corresponding offset will be experienced with regard to the laser energy emitted from the contact surface 4 of member 10 while the perpendicular orientation of the input surface results in a symmetric generally forward axial radiation pattern.

A guide wire slot or channel 10B is provided within the contact member through which a guide wire 14, discussed in more detail below, may be passed. The channel is oriented parallel to the longitudinal optical fiber and contact member axis, but offset or eccentric therefrom to minimize the direct laser irradiation of the guide wire which, in turn, could damage or sever the wire.

An infrared coating may be placed on the contact surface 4 to partially absorb, thereby converting to heat, the laser energy emanating therefrom. In this manner, lesions and plaque deposits may be excised by the dual-phase operation of the contact member which includes the direct action of the heated contact surface 4 as well as the indirect action of the laser energy irradiated into the offending tissue undergoing treatment.

Housing 12 defines a large diameter region 12A and a small diameter region 12B. The contact member 10 is affixed to the distal end of the wide region of the housing by means of, for example, a heat resistant adhesive or, alternatively, by mechanical crimping action, or both. A channel 12C is provided through the housing, and aligned with the contact member channel 10B, thereby to admit passage of the guide wire 14.

Referring again to FIG. 1, a multiple lumen catheter conduit 16 interconnects the distal radiation assembly 3 with the sources of fluid and laser energy, for example, with the laser generator source 24. Catheter conduit 16 is preferably extruded or otherwise fabricated from a flexible plastic material and may include two or more lumens or channels therein. The depicted catheter conduit comprises three lumens designated, respectively, 16A, 16B, and 16C. A plurality of individual conduits 18A,B,C are affixed to proximal or input ends of corresponding lumens 16A,B,C thereby to form gas or liquid tight connections thereto.

A flexible laser optical fiber 22 is positioned within the first lumen 16A and couples laser energy from laser generator source 24 to the input face 10A of contact member 10. Lumen 16A is preferably oriented along the central longitudinal axis of the catheter conduit 16 to facilitate the coupling of laser energy into the center of the contact member input surface. More specifically, the small diameter region 12B of the housing is inserted into the distal end of lumen 16A and serves to receive the end of the optical fiber 22 therethrough.

A fluid coupler 20 is affixed to the second end of conduit 18A thereby permitting the introduction of liquids (at inlet 20A), for example a saline solution W, into catheter lumen 16A (between the optical fiber 22 and lumen sidewall). The saline solution, thus admitted, travels the length of the catheter conduit; fills the interior region of housing 12, thereafter, exiting the laser catheter through housing channel 12C or, alternatively, through contact member channel 10B. The positive flow of solution through and outwardly from the distal end of the catheter precludes or minimizes the admission of blood or other contaminants to the interior region of housing 12 while simultaneously providing housing and contact member cooling.

It will be appreciated that the flow of cooling fluid can be admitted to the radiation assembly 3 in alternative ways, for example, through the use of a separate catheter conduit lumen. It will further be appreciated that the catheter conduit 16 may be extended and joined to the rear of housing 16 to thereby seal the interface therebetween against the entry or loss of fluid. In this manner, the potential for internal catheter contamination can be further limited.

The second lumen 16B serves as the passage for a guide wire 14 and is aligned with the corresponding contact member and housing channels 10B and 12C thereby to admit the substantially unrestricted passage of a guide wire 14 through the catheter conduit 16, housing 12, contact member 10, thereafter, outwardly through the artery or other narrow path forward of the laser catheter.

Figure 11A:
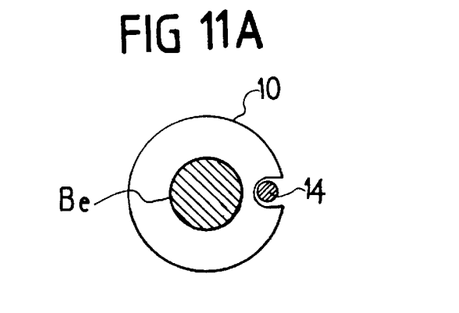
FIG. 11A is an end view of the distal end of the catheter, illustrating the physical relationship between the eccentrically positioned guide wire and the pattern of laser radiation.
Figure 11B:
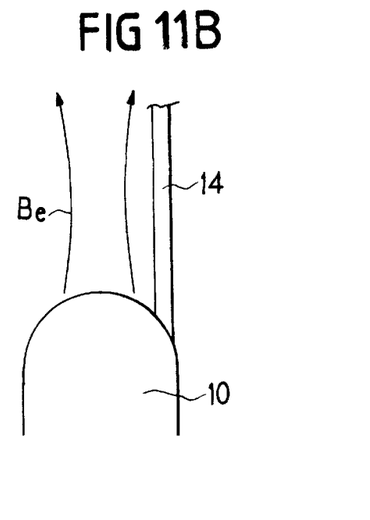
FIG. 11B is a side view of the distal end of the catheter, illustrating the physical relationship between the eccentrically positioned guide wire and the pattern of laser radiation.
Figure 12:
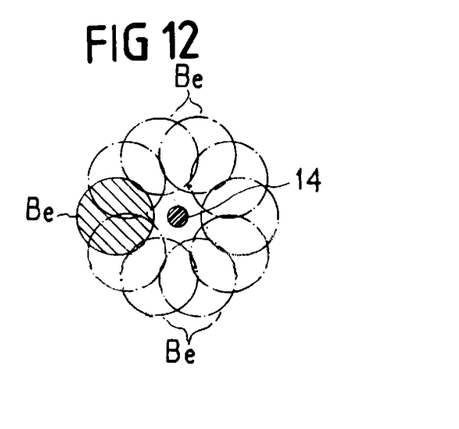
FIG. 12 illustrates a torus-shaped irradiation locus pattern available when using with an alternative off-axis configuration of the laser contact member of the present invention; and, FIG. 13 illustrates the positioning and use of the balloon angioplasty embodiment of the present invention in a diseased artery following the laser treatment thereof.

With specific reference to FIGS. 11A and 11B, it will be observed that the guide wire channel, by reason of its eccentric orientation with respect to the central axis of contact member 10, provides effective catheter guidance but, importantly, without significant exposure of the guide wire 14 to the laser energy, designated Be, and the concomitant risk of guide wire damage or severance.

Figure 9:
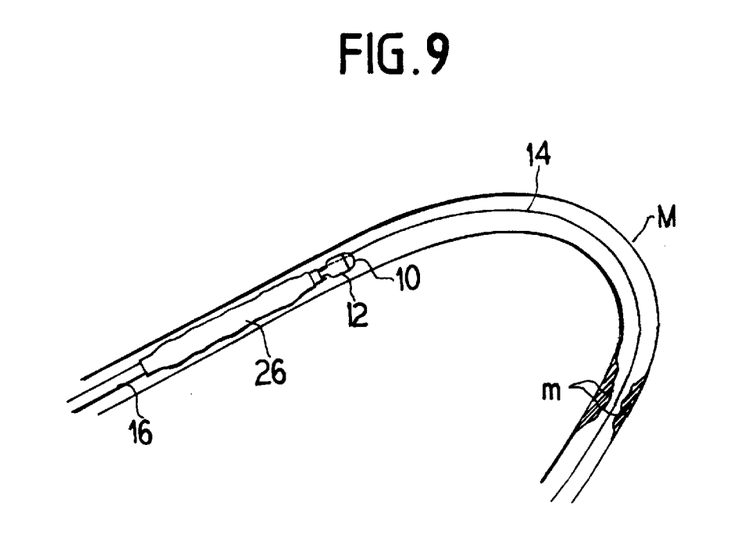
FIG. 9 is a schematic representation of the laser catheter of the present invention, including angioplasty balloon, shown positioned within a diseased artery with the guide wire extending beyond the point of arterial disease.

Use of the guide wire 14 to facilitate insertion and positioning of the present laser catheter is best illustrated in FIG. 9 wherein the catheter is shown during insertion into a narrow and curved artery M or similar narrow path having a partially occluded region "m" therein. The guide wire, being comparatively flexible, may be inserted ahead of the catheter, through curved or narrow passages, without significant likelihood of arterial damage or perforation. Once in position, i.e. with the guide wire bridging the occluded arterial region m (FIG. 9), the laser catheter can thereafter be urged along the guide wire further into the artery. As the catheter will tend to follow the guide wire, even through curved arterial regions, a substantially lowered exposure to arterial perforation results.

A third lumen 16C is in fluid communication with the interior of a balloon 26, the latter being positioned in fluid-tight relationship around the outer circumference of the catheter conduit 16 rearwardly of the radiation assembly 3. Liquid or gas pumped into the balloon 26 through lumen 16C expands the balloon as shown in FIG. 1.

Figure 10A:
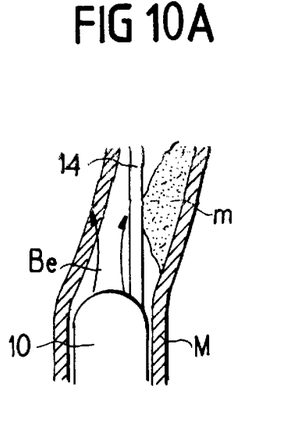
FIG. 10A illustrates placement of the laser catheter of the present invention in proximity to an area of arterial occlusion lying forward of the forward surface of the catheter in a portion of the lumen that has a longitudinal axis canted from the axis of the portion of the lumen in which the laser catheter is placed.
Figure 10B:
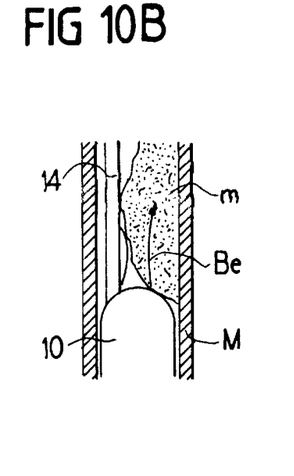
FIG. 10B illustrates placement of the laser catheter of the present invention in proximity to an area of arterial occlusion lying forward of the forward surface of the catheter in a portion of the lumen that has a longitudinal axis in line with the axis of that portion of the lumen in which the laser catheter is placed.

In operation the laser catheter of the present invention is used as follows. The guide wire 14 is first inserted into the artery or other narrow path until it extends beyond the area "m" requiring treatment. This is shown in FIG. 9. Thereafter, the catheter conduit 16 is urged progressively into the artery M until the radiation assembly 3 thereof is adjacent to, and preferably in abutting contact with, the arterial occlusion m, for example, as depicted in FIG. 10B.

Next, the laser source 24 is energized, generally for one second durations at 3–6 second intervals. The laser energy thus delivered to the contact surface 4, and radiated therefrom, substantially ablates the occlusion m thereby permitting further advancement of the catheter into the artery. This ablation process is referred to herein as the first mode of a dual-mode recanalization regime.

And to the extent that occlusion residue remains, the elevated temperatures of the contact member 10 and housing 12 sidewalls melt and reform such residue to further define the now enlarged or "recanalized" arterial opening. This melting reformation represents the second recanalization mode.

During the above described dual-mode recanalization process, water, or a saline solution thereof, are continuously passed outwardly through the radiation assembly 3 and, more specifically, outwardly through the contact member channel 10B to cool the radiation assembly and to minimize ingress of blood and other contaminants therein.

Figure 13:
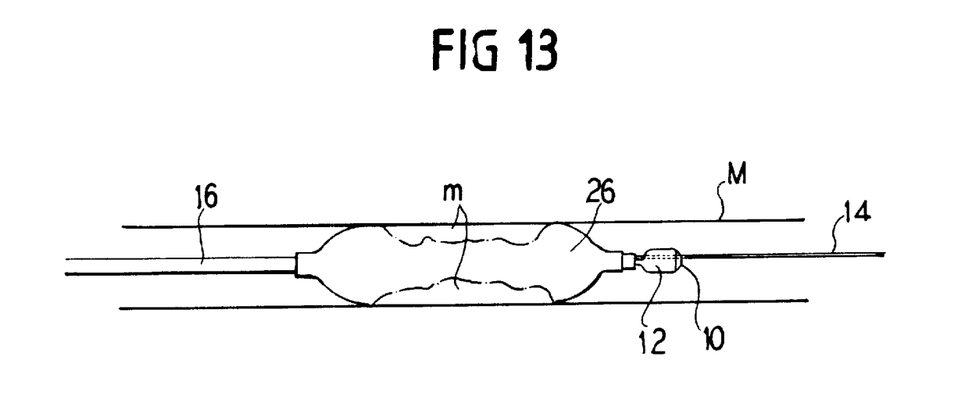

Upon completion of this dual-mode recanalization process, the laser catheter may be further advanced into the artery until the balloon 26, which is not yet expanded, is positioned as shown in FIG. 13 at the site "m" of lesion or plaque ablation. Thereafter, pressurized water or air is admitted to the balloon through lumen 16C which, in turn, expands the balloon further compressing the residual plaque outwardly against the arterial walls. Balloon pressure is subsequently relieved.

After completion of the above described recanalization process, the laser catheter can be advanced to the next site of arterial decease, or removed from the vessel undergoing treatment.

Figure 5:
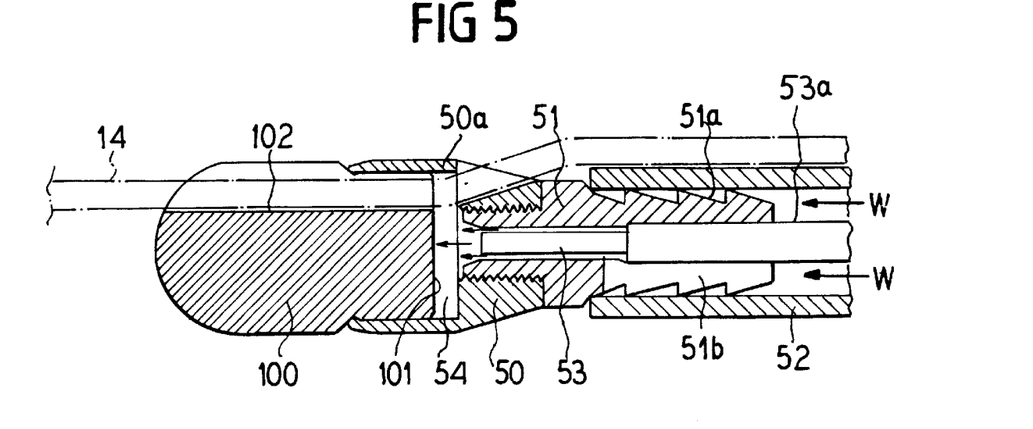
FIG. 5 is a front elevation view, taken in section, of the distal end of an alternative embodiment of the laser catheter of the present invention.
Figure 6:
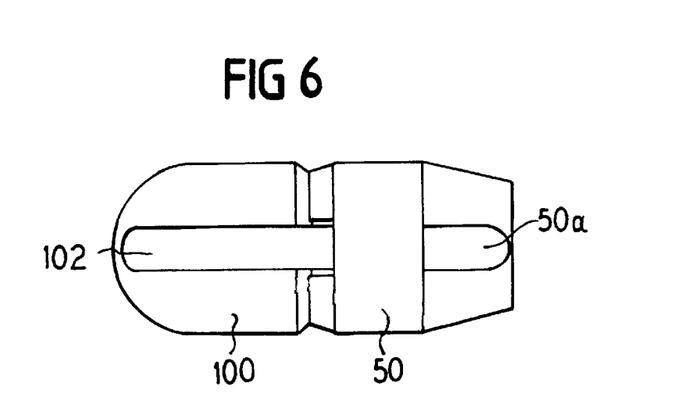
FIG. 6 is a plan view of the laser contact member and retention sleeve of the catheter of FIG. 5

An alternate embodiment of the present laser catheter is shown in FIGS. 5 and 6. This embodiment does not employ the balloon angioplasty option and utilizes a single lumen catheter conduit 52 through which the optical fiber 53, with its protective cover 53*a*, and cooling liquid W may be passed.

Referring to FIG. 5, a contact member 100 is retained, for example by crimping, within a generally cylindrical sleeve 50 which, in turn, is screwably received on one end of an interface nipple 51. Serrated projections 51a are provided along the other end of nipple 51 to facilitate the rigid retention of the nipple within the distal end of catheter conduit 52. Openings are provided along and through the center longitudinal axes of sleeve 50 and nipple 51 to receive the optical fiber therein and to permit the laser energy therefrom to be coupled into the contact member at its input surface 101. More specifically, the diameter of these openings is greater than that of the optical fiber thereby providing a path for the cooling liquid W, including slot 51*b* in nipple 51, to pass to the contact member 100, thereafter, outwardly through a guide wire channel 102 formed therein.

In the embodiment depicted in FIGS. 5 and 6, the guide wire 14 is routed through the artery or other narrow path externally to the laser catheter conduit 52, entering the catheter at the distal end thereof through an aperture 50*a* formed in the side of sleeve 50. Sleeve aperture 50*a* is aligned with the guide wire channel 102, which channel extends longitudinally along the side of contact member 100, thereby providing a path through which the guide wire may be extended forwardly of the laser catheter to achieve the benefits of catheter guidance previously considered.

The above described laser catheter operates in substantially the same manner as the catheter of FIG. 1 except that balloon angioplasty is not performed. Further, it will be appreciated that by not directing the guide wire through the catheter conduit, the guide wire need not extend the full length of the catheter and may, therefore, be of shorter length than the corresponding guide wire used in connection with the laser catheter of FIG. 1.

Figure 7:
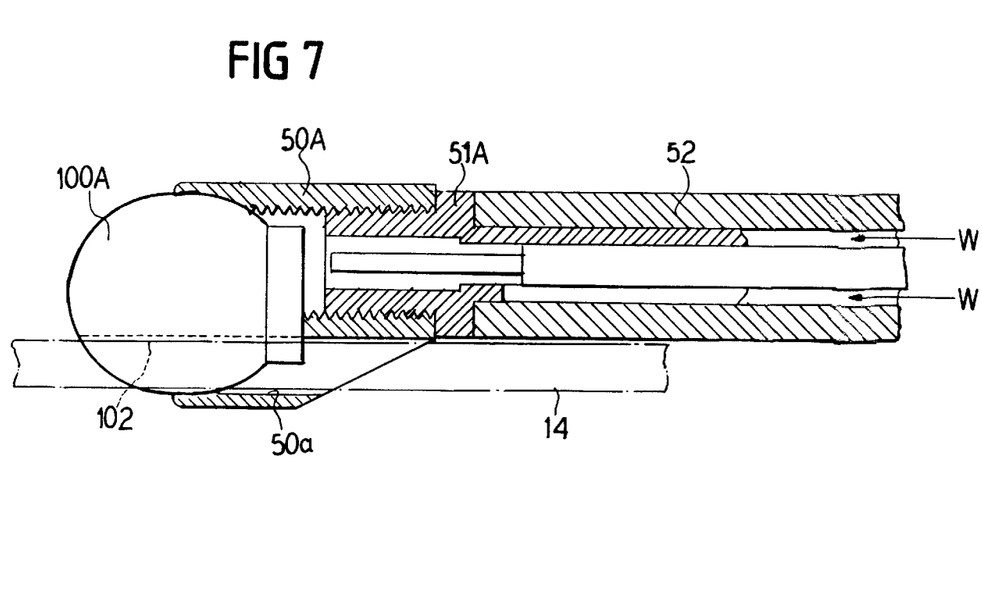
FIG. 7 is a front elevation view, taken partially in section, of the distal end of yet another embodiment of the laser catheter of the present invention.
Figure 8:
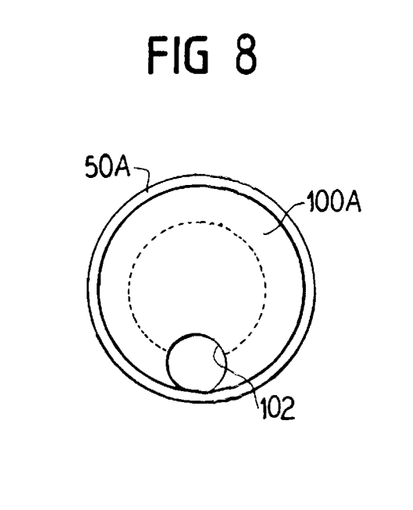
FIG. 8 is a left elevation view of the catheter of FIG. 7 illustrating the eccentric guide wire channel therethrough.

FIGS. 7 and 8 illustrate another embodiment of the present invention generally similar to the external guide wire approach discussed with reference to FIGS. 5 and 6 except that the optical fiber and catheter conduit are offset with respect to the sleeve 50A and contact member 100A to provide a straight channel 50*a,*102 through which the guide wire 14 may pass without bending. This arrangement minimizes the risk of guide wire buckling where, in particular, extremely fine and flexible guide wires are employed.

We claim:

1. A laser catheter for treatment of biological materials within arteries or other narrow passages of living organisms comprising:

a substantially non-thermally conductive, non-metallic optically transparent dual-phase contact member having a planar laser energy input surface at a proximal end of the contact member and a generally rounded laser output surface at a distal end of the contact member for contacting biological material and outputting laser energy opposed to the input surface;

a catheter conduit having at least one lumen;

a housing member for rigidly retaining said contact member and coupling the contact member to said catheter conduit; and an optical fiber positioned within one of the at least one conduit lumen, having an input end and an output end, said input end adapted for coupling to a source of laser energy and said output end having a generally planar output surface and disposed adjacent and in operative proximity to the contact member input surface, the contact member input surface disposed at an angle to the optical fiber output surface;

whereby laser energy, emitted from said output surface of the optical fiber, propagates in a path generally normal to and forward of said output surface and couples into the contact member at the contact member input surface, the input surface canting the laser energy path resulting in laser energy emitting from the contact surface at an angle to the laser energy path emitted from the optical fiber and impinging biological material residing along walls of the narrow passages surrounding the catheter.

2. A laser catheter for treatment of biological material within arteries or other narrow passages of living organisms comprising;

a catheter conduit of a slimness and flexibility suitable for insertion into a narrow bodily passage, said conduit having at least one lumen therein through which an optical fiber may pass, an optical fiber within the conduit lumen and having an output end, the fiber having a longitudinal axis, a distal member disposed substantially in front of the fiber, the distal member also having a longitudinal axis, and a housing member for mounting and retaining the distal member to an end of the catheter conduit, the distal member being a substantially non-thermally conductive, non-metallic, optically transmissive member having a generally rounded energy output surface on a forward end thereof and a laser energy input surface on an opposed rearward end thereof, distal member input surface disposed at an angle to and in operative proximity with the output end of the optical fiber whereby laser energy emitted from the output end of the optical fiber is coupled into the distal member such that a path defined by the laser energy as said laser energy propagates through the contact member deviates from a path defined by the laser energy as said laser energy is emitted from said optical fiber when said laser energy couples into the contact member at the contact member input surface, thereby rendering such laser energy emitted from said contact surface suitable for treating the surrounding walls of said narrow bodily passage.

3. The laser catheter of claim 2 further comprising a guide wire recess in the contact member, said recess being disposed generally parallel to, and offset from, the longitudinal axis of the contact member whereby laser damage to a guide wire extending through the contact member is avoided.

4. A laser catheter for treatment of biological material within arteries or other narrow passages of living organisms, comprising:

a substantially non-thermally conductive, non-metallic optically transparent dual-phase contact member having a generally rounded energy output surface on a forward end thereof and a laser energy input surface on an opposed rearward end thereof, said contact member including an optical energy absorbing coating on the output surface for absorbing a portion of laser energy input to said contact member and converting said laser energy to heat energy, the heat energy being emitted from the output surface, said contact member simultaneously emitting a portion of laser energy input thereto directly from the output surface for direct irradiation of an object to be treated, the heat energy and the laser energy being emitted from substantially identical regions of the output surface;

a catheter conduit of a slimness and flexibility suitable for insertion into a narrow bodily passage, said conduit having at least one lumen therein through which an optical fiber may pass and having a retainer thereon for supporting said contact member;

a housing member for rigidly retaining and mounting the contact member to an end of the catheter conduit; and an optical fiber within said conduit lumen, the optical fiber including an output end extending into said retainer in operative proximity to the contact member input surface;

the contact member input surface disposed at an angle to the optical fiber output end whereby laser energy emitted from the optical fiber output end in a path generally normal to and forward of the output end of the fiber deviates from the path as said laser energy couples into the contact member through the contact member input surface thereby rendering such laser energy emitted from said output surface suitable for treating the surrounding walls of said narrow bodily passage.

5. The laser catheter of claim 4 further comprising a guide wire recess in the contact member, said recess being disposed generally parallel to, and offset from, the longitudinal axis of the contact member whereby laser damage to a guide wire extending through the contact member is avoided.

6. The laser catheter of claim 4 wherein the longitudinal axis of the contact member is offset from a longitudinal axis of the optical fiber.

7. The laser catheter of claim 4 wherein the center longitudinal axis of the contact member is askew from a longitudinal axis of the optical fiber.

8. A laser catheter for treatment of biological material within arteries or other narrow passages within living organisms, comprising:

a substantially non-thermally conductive, non-metallic optically transparent dual-phase contact member having a generally round energy output surface on a forward end thereof and a laser energy input surface on an opposed rearward end thereof, said contact member including an optical energy absorbing coating on the output surface for absorbing a portion of laser energy input to said contact member and converting said laser energy to heat energy, the heat energy being emitted from the output surface, said contact member simultaneously emitting a portion of laser energy input thereto directly from the output surface for direct irradiation of an object to be treated, the laser energy emitted from the contact member passing through at least that portion of the output surface which contacts the object to be treated;

a catheter conduit of a slimness and flexibility suitable for insertion into a narrow bodily passage, said conduit having at least two lumens therein;

an optical fiber within a first conduit lumen, the optical fiber including an end in operative proximity to the contact member input surface;

the contact member input surface disposed at an angle to the optical fiber output end such that a path defined by the laser energy as said laser energy propagates through the contact member deviates from a path defined by the laser energy as said laser energy is emitted from said optical fiber when said laser energy couples into the contact member at the contact member input surface, thereby rendering such laser energy emitted from said contact surface suitable for treating the surrounding walls of said narrow bodily passage;

housing means for rigidly retaining and mounting said contact member to an end of the catheter conduit the housing means and contact member having a central longitudinal axis defined therethrough; and a guide wire recess in the housing means and contact member, said recess being disposed generally parallel to, and offset from, the longitudinal axis whereby laser damage to a guide wire extending through the housing means and contact member is avoided; a second lumen in the catheter conduit for the passage of a guide wire therethrough, said second lumen disposed in generally collinear relationship to the housing means and contact member guide wire recess whereby a guide wire may be inserted, and subsequently removed, through the catheter conduit, the housing means, and contact member guide wire recess to permit the wire to be extended forwardly of the laser catheter to facilitate positioning of the laser catheter through curved or tight paths.

9. A laser catheter for treatment of biological material within arteries or other narrow passages within living organisms comprising:

a substantially non-thermally conductive, non-metallic optically transparent dual-phase contact member having a generally rounded energy output surface on a forward end thereof and a laser energy input surface on an opposed rearward end thereof, said contact member including an optical energy absorbing coating on the output surface for absorbing a portion of laser energy input to said contact member and converting said laser energy to heat energy, the heat energy being emitted from the output, said contact member simultaneously emitting a portion of laser energy input thereto directly from the output for direct irradiation of an object to be treated, the heat energy and the laser energy being emitted from substantially identical regions of the output surface;

a catheter conduit of a slimness and flexibility for insertion into a narrow bodily passage, said conduit said conduit having at least one lumen therein through which an optical fiber and cooling fluid may pass and having a retainer thereon for supporting said contact member;

an optical fiber within the conduit lumen, the optical fiber including an output end extending into said retainer in operative proximity to the contact member input surface whereby laser energy from the optical fiber is coupled into the contact member; and a housing means for rigidly retaining and mounting said contact member to an end of the catheter conduit;

the contact member input surface disposed at an angle to the optical fiber output end such that a path defined by the laser energy as said laser energy propagates through the contact member deviates from a path defined by the laser energy as said laser energy is emitted from said optical fiber when said laser energy couples into the contact member at the contact member input surface, thereby rendering such laser energy emitted from said contact surface suitable for treating the surrounding walls of said narrow bodily passage.

10. The laser catheter of claim 9 wherein the longitudinal axis of the contact member is offset from a longitudinal axis of the optical fiber.

11. The laser catheter of claim 9 further comprising a guide wire recess in the contact member, said recess being disposed generally parallel to, and offset from, the longitudinal axis of the contact member whereby laser damage to a guide wire extending through the contact member is avoided.

12. The laser catheter of claim 4 wherein the center longitudinal axis of the contact member is askew from a longitudinal axis of the optical fiber.

13. A laser catheter for treatment of biological material within arteries or other narrow passages of living organisms, comprising:

a substantially non-thermally conductive, non-metallic optically transparent dual-phase contact member having a generally rounded energy output surface on a forward end thereof and a laser energy input surface on an opposed rearward end thereof, said contact member including an optical energy absorbing coating on the output surface for absorbing a portion of laser energy input to said contact member and converting said laser energy to heat energy, the heat energy being emitted from the output surface, said contact member simultaneously emitting a portion of laser energy input thereto directly from the output surface for direct irradiation of an object to be treated, the laser energy emitted passing through at least that portion of the output surface which contacts the object to be treated;

a catheter conduit of a slimness and flexibility suitable for insertion into a narrow bodily passage, said conduit having at least one lumen therein through which an optical fiber may pass;

a housing member for rigidly retaining and mounting the contact member to an end of the catheter conduit; and an optical fiber within the conduit lumen, the optical fiber including an output end in operative proximity to the contact member input surface whereby laser energy from the optical fiber is coupled into the contact member; the contact member input surface disposed at an angle to the optical fiber output end such that a path defined by the laser energy as said laser energy propagates through the contact member deviates from a path defined by the laser energy as said laser energy is emitted from said optical fiber when said laser energy couples into the contact member at the contact member input surface, thereby rendering such laser energy emitted from said contact surface suitable for treating the surrounding walls of said narrow bodily passage.

14. A laser catheter for treatment of biological material within arteries or other narrow passages within living organisms, comprising:

a substantially non-thermally conductive, non-metallic optically transparent dual-phase contact member having a generally rounded energy output surface on a forward end thereof and a laser energy input surface on an opposed rearward end thereof, said contact member including an optical energy absorbing coating on the output surface for absorbing a portion of laser energy input to said contact member and converting said laser energy to heat energy, the heat energy being emitted from the output surface, said contact member simultaneously emitting a portion of laser energy input thereto directly from the output surface for direct irradiation of an object to be treated, the heat energy and the laser energy being emitted from substantially identical regions of the output surface;

a catheter conduit of a slimness and flexibility suitable for insertion into a narrow bodily passage, said conduit having at least two lumens therein and having a retainer thereon for supporting said contact member;

an optical fiber within a first conduit lumen, the optical fiber including an output end extending into said retainer in operative proximity to the contact member input surface;

the contact member input surface disposed at an angle to the optical fiber output end such that a path defined by the laser energy as said laser energy propagates through the contact member deviates from a path defined by the laser energy as said laser energy is emitted from said optical fiber when said laser energy couples into the contact member at the contact member input surface, thereby rendering such laser energy emitted from said contact surface suitable for treating the surrounding walls of said narrow bodily passage;

housing means for rigidly retaining and mounting said contact member to an end of the catheter conduit, the housing means and contact member having a central longitudinal axis defined therethrough; and a guide wire recess in the housing means and contact member, said recess being disposed generally parallel to, and offset from, the longitudinal axis whereby laser damage to a guide wire extending through the housing means and contact member is avoided; a second lumen in the catheter conduit for passage of a guide wire therethrough, said second lumen disposed in generally collinear relationship to the housing means and contact member guide wire recess whereby a guide wire may be inserted, and subsequently removed, through the catheter conduit, the housing means, and contact member guide wire recess to permit the wire to be extended forwardly of the laser catheter to facilitate positioning of the laser catheter through curved or tight paths.

15. The laser catheter of claim 14 wherein the center longitudinal axis of the contact member is askew from a longitudinal axis of the optical fiber.

16. The laser catheter of claim 4, including a balloon external and affixed in fluid-tight engagement with the catheter conduit; and a third conduit lumen in fluid communication with the balloon whereby the balloon may be expanded and contracted through the application and removal of pressurized fluid to the third lumen.

17. The laser catheter of claim 14 wherein the longitudinal axis of the contact member is offset from a longitudinal axis of the optical fiber.

18. The laser catheter of claim 14 including a source of cooling fluid connected to a distal end of said first conduit for delivering a cooling fluid through the first conduit to said contact member.

19. The laser catheter of claim 18 in which the means for delivering a cooling fluid includes a separate catheter conduit fluid lumen, said fluid lumen having a distal end in fluid communication with the contact member and a proximal end into which fluid may be introduced, whereby fluid introduced into the proximal end of the lumen is communicated to, and cools, the contact member.

20. The laser catheter of claim 18 which the means for delivering a cooling fluid includes the first optical fiber lumen, said lumen defining a cross-section of area greater than that of the optical fiber therein and wherein said first lumen has a distal end in fluid communication with the contact member and a proximal end remote therefrom whereby fluid introduced into the proximal end of the first lumen is communicated to, and cools, the contact member.

21. The laser catheter of claim 18 wherein the housing means includes means bridging an end of the catheter conduit and contact member whereby substantially all of the cooling fluid delivered through the catheter conduit passes outwardly from the laser catheter through the contact member guide wire recess.

22. A laser catheter for treatment of biological material within arteries or other narrow passages within living organisms, comprising:

a substantially non-thermally conductive, non-metallic optically transparent dual-phase contact member having a generally round energy output surface on a forward end thereof and a laser energy input surface on an opposed rearward end thereof, said contact member including an optical energy absorbing coating on the output surface for absorbing a portion of laser energy input to said contact member and converting said laser energy to heat energy, the heat energy being emitted from the output surface, said contact member simultaneously emitting a portion of laser energy input thereto directly from the output surface for direct irradiation of an object to be treated, the laser energy emitted passing through at least that portion of the output surface which contacts the object to be treated;

a catheter conduit of a slimness and flexibility suitable for insertion into a narrow bodily passage, said conduit having at least one lumen therein through which an optical fiber and cooling fluid may pass;

housing means for rigidly retaining and mounting the contact member to an end of the catheter conduit; and an optical fiber within the conduit lumen, the optical fiber including an output end in operative proximity to the contact member input surface whereby laser energy from the optical fiber is coupled into the contact member; the contact member input surface disposed at an angle to the optical fiber output end such that a path defined by the laser energy as said laser energy propagates through the contact member deviates from a path defined by the laser energy as said laser energy is emitted from said optical fiber when said laser energy couples into the contact member at the contact member input surface, thereby rendering such laser energy emitted from said contact surface suitable for treating the surrounding walls of said narrow bodily passage.

* * * * *